United States Patent
Glenneberg et al.

(12)

(10) Patent No.: US 6,399,795 B1
(45) Date of Patent: Jun. 4, 2002

(54) METHOD FOR PRODUCING 2-(4-METHYL-3-PENTENYL) ANTHRAQUINONE

(75) Inventors: Jürgen Glenneberg, Offenbach; Holger Sauerstein, Gelnhausen, both of (DE); Hubert Angert, Coqueiral-Arancruz (BR)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/910,956

(22) Filed: Jul. 24, 2001

(30) Foreign Application Priority Data

Aug. 4, 2000 (DE) .......................................... 100 38 101

(51) Int. Cl.⁷ .................... C07C 45/27; C07C 46/00; C07C 50/18
(52) U.S. Cl. .................... 552/208; 552/268; 552/269; 552/270
(58) Field of Search ................. 552/208, 268, 552/269, 270

(56) References Cited

U.S. PATENT DOCUMENTS

| | | | | |
|---|---|---|---|---|
| 4,369,140 A | * | 1/1983 | Komatsu et al. | |
| 6,057,461 A | * | 5/2000 | Estanove et al. | |
| 6,127,580 A | * | 10/2000 | Siegel et al. | |

FOREIGN PATENT DOCUMENTS

| | | |
|---|---|---|
| DE | 198 16 297 A1 | 10/1999 |
| EP | 0 921 111 A1 | 6/1999 |
| FR | 2 111 190 | 6/1972 |

OTHER PUBLICATIONS

Japan 58–180452, Oct. 21, 1983, Shigeaki Numata.
Japan 59–51235, Mar. 24, 1984, Shigeaki Numata.
Methoden Der Organischen Chemie, Chinone, Teil III, 9,10–Anthrachinone, 10–Anthrone Und 1,9–Cycloanthrone–(10), Bayer et al, pp. 23–31.
International Search Report for corresponding European Appln No. EP 01 11 3460 dated Nov. 14, 2001.
Patent Abstracts of Japan, vol. 008, No. 015 for JP 58–180452 published Oct. 21, 1983.

* cited by examiner

*Primary Examiner*—Johann Richter
*Assistant Examiner*—Sikarl A. Witherspoon
(74) *Attorney, Agent, or Firm*—Smith, Gambrell & Russell, LLP

(57) ABSTRACT

A method for producing 2-(4-methyl-3-pentenyl) anthraquinone (IHEAQ) that includes a Diels-Alder addition of naphtho-1,4-quinone and myrcene and an oxidation of the resulting adduct. The oxidation step is carried out in the presence of a solvent mixture that contains a polar and a nonpolar solvent. The oxidation takes place with air or an $O_2$-containing gas in the presence of a combination of a strong inorganic base and an organic, especially a nitrogen-containing base. The method leads to a higher space-time yield and higher product purity.

23 Claims, No Drawings

METHOD FOR PRODUCING 2-(4-METHYL-3-PENTENYL) ANTHRAQUINONE

INTRODUCTION AND BACKGROUND

The present invention relates to a method for obtaining 2-(4-methyl-3-pentenyl)anthraquinone, which is called 2-isohexenylanthraquinone (IHEAQ) herein, by oxidation of the adduct of naphthoquinone and myrcene formed by a Diels-Alder reaction.

Anthraquinones can be prepared in accordance with Houben-Weyl, Methods of Organic Chemistry, $4^{th}$ edition, Volume VII/3c, Georg Thieme Verlag, Stuttgart, 1979, pp. 23–31, and Volume VII/2b, pp. 1765 ff., by thermally reacting a diene with naphthoquinone in a first step. This Diels-Alder addition is usually carried out in a solvent, but it can also take place directly by heating the components. However, it can be managed by using catalyst like Lewis acids such as boron trifluoride.

In a next step, the Diels-Alder adduct is converted to anthraquinone in the presence of alkali metal hydroxides and air via the intermediate step of the 1,4-dihydroanthraquinone compound. According to Japanese published patent applications JP-A 58-180452 and JP-A 59-51235, 2-isohexenylanthraquinone can be prepared from myrcene and naphthoquinone. In this method, the Diels-Alder adduct formed from these substances is oxidized with air in aqueous ethanol in the presence of an alkali hydroxide; the resulting yellow 2-isohexenylanthraquinone precipitates from the reaction mixture and can be isolated from it and recrystallized in a known way.

The known method for producing 2-isohexenylanthraquinone (IHEAQ) has the disadvantage that the IHEAQ formed during oxidation precipitates from the solution before the end of complete oxidation with air. Because of this, especially when the process is carried out on a larger scale, it becomes difficult to mix the reaction mixture. Also, the delivery of air or oxygen is hindered and thus the reaction time up to quantitative conversion is considerably increased. The mixing problem can be alleviated by using a larger amount of solvent, but this reduces the space-time yield. Another disadvantage of the previously known method is that the precipitated IHEAQ includes the unreacted educt, intermediate products and alkali hydroxide, which leads to a product of reduced purity. In addition, the included components can lead to problems in the further use of the IHEAQ, for example, when it is used as a reaction carrier in the anthraquinone method for producing hydrogen peroxide; in order to avoid these problems, up to now the IHEAQ has had to be recrystallized and washed with an acid at high expense.

It is therefore an object of this invention to produce 2-isohexenylanthraquinone in a way that overcomes the problems of the prior art. The improved method of the present invention is intended on the one hand to lead to a higher space-time yield, and on the other to produce a product of higher purity.

SUMMARY OF THE INVENTION

The above and other objects of the present invention can be achieved by a method for producing 2-(4-methyl-3-pentenyl)anthraquinone (IHEAQ) that includes a Diels-Alder addition, where naphtho-1,4-quinone is reacted with myrcene [7-methyl-3-methylene-1,6-octadiene], and an oxidation of the resulting Diels-Alder adduct [2-(4-methyl-3-pentenyl)-1,4,11,12-tetrahydroanthraquinone] with an oxygen-containing gas in an organic solvent in the presence of a base, which is characterized by the fact that the oxidation is carried out in a solvent mixture containing a polar and a nonpolar organic solvent in the presence of a strong inorganic and an organic base.

As the examples and comparison examples illustrate, the conversion in the oxidation of the Diels-Alder adduct 2-(4-methyl-3-pentenyl)-1,4,11,12-tetrahydroanthraquinone to 2-isohexenylanthraquinone can be increased by using a combination of a strong inorganic base, such as sodium hydroxide, and an organic amine. The increase of conversion brought about by the combination of bases is surprisingly achieved independently from the solvent or solvent mixture. A particularly high increase of conversion can be brought about by using, in addition to the said combination of bases, a combination of solvents that contains both a polar and a nonpolar solvent. This particularly preferred embodiment, oxidation in the presence of the said combination of bases and combination of solvents, results in no precipitation occurring during the oxidation, the conversion being accelerated, and no undesirable byproducts being contained in the 2-isohexenylanthraquinone.

DETAILED DESCRIPTION OF THE INVENTION

The sources of the problems that are present in the prior art and the overcoming of them in accordance with the invention can be explained as follows:

In the reaction of the Diels-Alder adduct, hydroquinones or their salts arise as intermediate steps to IHEAQ. These substances are quite readily soluble in polar solvents, but poorly soluble in nonpolar solvents. On the other hand, the Diels-Alder adduct and the end product IHEAQ are more soluble in nonpolar solvents than in polar solvents. Strong inorganic bases are reasonably priced, but not very effective because of their low solubility in nonpolar solvents. Organic bases are more expensive, but they are readily soluble in polar as well as nonpolar solvents. The use of a nonwater-miscible nonpolar solvent simplifies the subsequent processing steps, such as separation of the bases by washing with an acid.

Aliphatic, cycloaliphatic, aromatic, and aromatic-aliphatic hydrocarbons are especially suitable as nonpolar solvents. Among the aliphatic hydrocarbons, branched and unbranched hydrocarbons with 6–12 carbon atoms, especially 6–10 carbon atoms, thus hexane, heptane, octane and decane and mixtures of such hydrocarbons, are especially suitable. Among the cycloaliphatic hydrocarbons, cyclohexane and terpene hydrocarbons should be particularly emphasized. Among the aromatics and alkyl-substituted aromatic compounds, benzene and methylated benzenes like toluene, xylenes, trimethylbenzenes, tetramethylbenzenes and mixtures of such mothylated benzenes are particularly suitable; instead of or in addition to methyl groups, the benzene ring can also have other lower alkyl groups like ethyl, n-propyl and isopropyl. Mixtures of alkylated, especially methylated, benzenes are commercially available.

The following are possibilities as polar solvents: alcohols, in particular ethanol, n-propanol, isopropanol, n-butanol, isobutanol, octanol and diisobutylcarbinol; esters, in particular acetates and propionates, for example ethyl acetate and methyl cyclohexyl acetate, alkyl phosphates like tris-(2-ethylhexyl) phosphate; amides, N-alkylamides, N-alkylpyrrolidones, N,N-dialkylcarbamates, N-alkylcaprolactams as well as alkylated ureas, especially tetraalkylated ureas. In the case of the said N-alkylated compounds, alkyl preferably stands for a linear alkyl group with 1–8 C atoms, for example N-methylcaprolactam, N-hexylcaprolactam, N-octylcaprolactam, N-methylpyrrolidone, tetramethyl urea and tetrabutyl urea.

The solvent mixture that is to be used in the preferred embodiment can contain one or more polar and one or more nonpolar solvents. The ratio of the amounts of nonpolar solvents to polar solvents can vary in a wide range; the weight ratio is in general in the range from 5 to 1 up to 1 to 5. Preferably, the weight fraction of nonpolar solvents is higher than that of the polar solvents; according to one particularly preferred embodiment, the weight ratio of polar to nonpolar solvents lies in the range from 1 to 2 up to 1 to 4.

Preferably one or more bases from among lithium, sodium and potassium hydroxides or aqueous solutions of these hydroxides are used as strong inorganic bases.

The bases to be used are preferably nitrogen-containing bases. In particular, primary, secondary and tertiary aliphatic and cycloaliphatic amines can be used, where these amines can be mono-, di- and triamines. Preferably, the amines contain 2–10 carbon atoms. Examples of these said amines are ethylamine, diethylamine, triethylamine, mono-, di- and tripropyl amine or mono-, di- and tributylamine, ethylenediamine, diethylenetriamine, morpholine, N-methylmorpholine, isophoronediamine and bicyclic amines like 1,4-diazabicyclo-2,2,2-octane and amidines like DBU (1,8-diazabicyclo-(5.4.0)-undec-7-ene). Effective organic bases also include guanidines and alkyl guanidines, such as tetramethyl guanidine in particular. Quaternary ammonium hydroxides and salts can also be used, since the latter convert to the corresponding hydroxide in the presence of alkali hydroxides; examples are tetramethyl and especially tetrabutyl ammonium hydroxide and salts of these bases with mineral acids.

In general, 0.01–5 mol, especially 0.02–0.5 mol of the combination of organic and inorganic bases is used per mol of Diels-Alder adduct. The ratio of the amounts of inorganic or organic base is variable in a wide range, but usually the inorganic base is used in a higher amount. Usually, the mol ratio of inorganic base to organic base lies in the range of 1 to 4 up to 4 to 1, especially 1 to 1 up to 3 to 1.

The substantially known reaction of myrcene with naphthoquinone takes place by heating the components in the presence or absence of a solvent at, usually, 50–200° C., preferably 50–120° C. In this first step any solvents can be used, but the solvent mixture that is used in the second step, thus the oxidation step, is preferred. The products myrcene and 1,4-naphthoquinone are used in a stoichiometric ratio, but myrcene can be used in an excess or in a deficient amount. The Diels-Alder addition is preferably carried out in the absence of a catalyst, but the use of a catalyst like a Lewis acid, for example boron trifluoride, is possible.

The Diels-Alder adduct, provided it is not in the form of a solution, is dissolved in a solvent mixture in accordance with the invention, which contains at least one polar and one nonpolar solvent. According to a particularly preferred embodiment, the solvent mixture is composed so that it forms an azeotrope—this considerably simplifies the further processing by distillation. After the addition of the combination of an inorganic and an organic base in accordance with the invention, the oxidation of the Diels-Alder adduct takes place with an oxygen-containing gas, especially air or pure oxygen that is supplied to the solution at a pressure of 0.5 bar to 100 bar (absolute), preferably in the range of 1–10 bar (absolute). Oxygen is preferred as oxidation agent. The oxidation is carried out at a temperature in the range from 20–200° C., preferably 50–150° C. The oxidation step can be carried out in conventional reaction equipment, for example a stirred vessel with gas injection, a loop reactor, or a bubble column with or without internal fittings.

After the end of the conversion the base can be separated from the reaction mixture, for example by washing with water and/or an acid or the bases can be separated from the reaction mixture by means of an ion exchanger. Further processing and purification of the 2-isohexenylanthraquinone can take place after separation of the solvent mixture—preferably it is separated by distillation—by recrystallization and/or distillation or by treating the solution with an adsorption agent like aluminum oxide or activated carbon.

The method in accordance with the invention is characterized by a high space-time yield and high product purity. Because of the improved method and the resulting higher purity of the 2-isohexenylanthraquinone, it is also possible to send the IHEAQ dissolved in the solvent mixture directly to further application. Provided one uses a solvent mixture as is conventional in the anthraquinone process for producing hydrogen peroxide, and IHEAQ is a carrier of the reaction of this process, the reaction mixture obtained in the oxidation step in accordance with the invention can be added directly to the working solution of the anthraquinone process.

The following examples and comparison examples illustrate the carrying out of the method of the invention as well as the advantages that result from it.

EXAMPLES 70 mmol of the Diels-Alder adduct 2-(4-methyl-3-pentenyl)-1,4,11,12-tetrahydroanthraquinone, obtained from 1,4-naphthoquinone and myrcene, were dissolved in 80 mL solvent or solvent mixture at 70° C. in a double-jacketed vessel with gas injection stirrer; the given base or base combination is added and the solution was oxidized for 1 h with oxygen. The reaction mixture was analyzed by HPLC. The amounts that were used and the space-time yield follow from the table. The number after the solvent gives the volume fraction in the solvent mixture. The number after the base gives the amount used in mmol.

No precipitation occurred in any of the tests during the reaction with the base, and the reaction mixture remained liquid even after cooling to room temperature.

TABLE

| Example No. | Nonpolar solvent | Polar solvent | Inorganic base | Organic base | Conversion of Diels-Alder adduct to IHEAQ after 1 h of reaction time (mol %) |
|---|---|---|---|---|---|
| 1 *) | Toluene 100 | — | — | Diethylamine 7 | 36 |
| 2 *) | Toluene 100 | — | NaOH 14 | — | 2 |
| 3 *) | Toluene 100 | — | NaOH 14 | Diethylamine 7 | 57 |
| 4 *) | Toluene 75 | n-Butanol 25 | NaOH 14 | — | 35 |
| 5 *) | Toluene 75 | n-Butanol 25 | — | Diethylamine 7 | 58 |
| 6 **) | Toluene 75 | n-Butanol 25 | NaOH 14 | Diethylamine 7 | 100 |

*) example not in accordance with the invention
**) example in accordance with the invention

EXAMPLE 7

Not in Accordance With the Invention 70 mmol Diels-Alder adduct and 14 mmol NaOH (as a 3.5 mmol aqueous solution) were reacted with oxygen as described above in pure n-butanol as solvent. The Diels-Alder adduct was converted to IHEAQ after only a short time, but a flaky precipitate formed. The reaction mixture was solid upon cooling to under 60° C. and could be processed further only with difficulty.

EXAMPLE 8

The current best embodiment of the overall process is given below.

850 g naphthoquinone (95%) is present in a mixture of 4000 mL toluene and 1300 mL n-butanol, and a total of 990 g myrcene (79%) is added while heating to 90° C. After 5 h, the reaction to Diels-Alder adduct is stopped. A yield of Diels-Alder adduct of 92% (with respect to reacted naphthoquinone) is determined.

The solution of the Diels-Alder adduct is cooled to 70° C.; then 250 mL water, 52 mL 50% sodium hydroxide and 50 mL diethylamine are added. The solution is then treated by passing oxygen gas through it at 70° C. After 5 h, the oxygen adsorption is ended. HPLC measurement shows complete conversion to IHEAQ (the aqueous phase is separated, the organic phase is washed with water and dilute phosphoric acid). The solvents are distilled out, the residue of IHEAQ is purified by distillation. Pure IHEAQ is obtained in 87% yield and over 96% purity.

Further variations and modifications of the present invention will be apparent to those skilled in the art from the foregoing and are intended to be encompassed by the claims appended hereto.

German priority application 100 38 101.4 of Aug. 4, 2000 is relied on and incorporated herein by reference.

What is claimed is:

1. A method for producing 2-(4-methyl-3-pentenyl) anthraquinone (IHEAQ), which comprises carrying out a Diels-Alder addition reaction, wherein naphtho-1,4-quinone is reacted with myrcene [7-methyl-3-methylene-1,6-octadiene] to produce a Diels-Alder adduct which is [2-(4-methyl-3-pentenyl)-1,4,11,12-tetrahydroanthraquinone] and then oxydizing said adduct with an oxygen-containing gas in an organic solvent in the presence of a base, said oxidizing being carried out in a solvent mixture containing a polar and a nonpolar organic solvent in the presence of a strong inorganic base and an organic base.

2. The method according to claim 1, wherein said nonpolar solvent is an aliphatic, cycloaliphatic, aromatic and aromatic-aliphatic hydrocarbon.

3. The method according to claim 2, wherein said nonpolar solvent is an alkylated benzene selected from the group consisting of tolunes, xylenes, trimethylbenzenes, tetramethylbenzenes and mixtures of alkylbenzenes.

4. The method according to claim 1, wherein said polar solvent is an alcohol, ester, phosphate, amide, N-alkylamide, N-alkylpyrrolidone, N,N-dialkylcarbamate, alkylated urea or N-alkylcaprolactam.

5. The method according to claim 2, wherein said polar solvent is an alcohol, ester, phosphate, amide, N-alkylamide, N-alkylpyrrolidone, N,N-dialkylcarbamate, alkylated urea or N-alkylcaprolactam.

6. The method according to claim 3, wherein said polar solvent is an alcohol, ester, phosphate, amide, N-alkylamide, N-alkylpyrrolidone, N,N-dialkylcarbamate, alkylated urea or N-alkylcaprolactam.

7. The method according to claim 4, wherein said solvent is selected from the group consisting of ethanol, n-propanol, n-butanol, octanol, diisobutyl carbinol, methyl cyclohexyl acetate, tris-(2-ethylhexyl) phosphate, tetramethyl and tetrabutyl urea, N-methylpyrrolidone and N-methyl-, hexyl- and octylcaprolactam.

8. The method according to claim 5, wherein said solvent is selected from the group consisting of ethanol, n-propanol, n-butanol, octanol, diisobutyl carbinol, methyl cyclohexyl acetate, tris-(2-ethylhexyl) phosphate, tetramethyl and tetrabutyl urea, N-methylpyrrolidone and N-methyl-, hexyl- and octylcaprolactam.

9. The method according to claim 6, wherein said solvent is selected from the group consisting of ethanol, n-propanol, n-butanol, octanol, diisobutyl carbinol, methyl cyclohexyl acetate, tris-(2-ethylhexyl) phosphate, tetramethyl and tetrabutyl urea, N-methylpyrrolidone and N-methyl-, hexyl- and octylcaprolactam.

10. The method according to claim 1, wherein lithium, sodium or potassium hydroxide or a mixture thereof or an aqueous solution of the alkali hydroxides is used as inorganic base.

11. The method according to claim 2, wherein lithium, sodium or potassium hydroxide or a mixture thereof or an aqueous solution of the alkali hydroxides is used as inorganic base.

12. The method according to claim 3, wherein lithium, sodium or potassium hydroxide or a mixture thereof or an aqueous solution of the alkali hydroxides is used as inorganic base.

13. The method according to claim 4, wherein lithium, sodium or potassium hydroxide or a mixture thereof or an aqueous solution of the alkali hydroxides is used as inorganic base.

14. The method according to claim 7, wherein lithium, sodium or potassium hydroxide or a mixture thereof or an aqueous solution of the alkali hydroxides is used as inorganic base.

15. The method according to claim 1, wherein said organic base is a member selected from the primary, secondary and tertiary aliphatic and cycloaliphatic mono-, di- and triamines, tetraalkylammonium hydroxides and salts, tetramethyl guanidine, 1,8-diazabicyclo-(5.4.0)-undec-7-ene and 1,4-diazabicyclo-2,2,2-octane.

16. The method according to claim 1, wherein one or more polar and one or more nonpolar solvents are used in a weight ratio in the range from 5 to 1 up to 1 to 5.

17. The method according to claim 1, wherein one or more polar and one or more nonpolar solvents are used in a weight ratio in the range from 1 to 2 up to 1 to 4.

18. The method according to claim 1, wherein 0.01–5 mol, of the combination of organic and inorganic bases is used per mol of Diels-Alder adduct.

19. The method according to claim 1, wherein 0.02–0.5 mol, of the combination of organic and inorganic bases is used per mol of Diels-Alder adduct.

20. The method according to claim 1, wherein the inorganic base and organic base are used in a mol ratio in the range from 1 to 4 up to 4 to 1.

21. The method according to claim 1, wherein the inorganic base and organic base are used in a mol ratio in the range from 1 to 1 up to 3 to 1.

22. The method according to claim 1, wherein the oxidation is carried out at 20–200° C., at a pressure of the supplied gases in the range of 1–10 bar (absolute) while using oxygen.

23. The method according to claim 1, wherein the oxidation is carried out at 50–150° C., at a pressure of the supplied gases in the range of 1–10 bar (absolute) while using oxygen.

* * * * *